(12) United States Patent
Garbergs et al.

(10) Patent No.: US 7,810,937 B2
(45) Date of Patent: Oct. 12, 2010

(54) CONTROL OF AN AUTOMATIC DARKENING FILTER

(75) Inventors: Bengt Garbergs, Falun (SE); Marcus Wiederkehr, Leksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/540,837

(22) Filed: Aug. 13, 2009

(65) Prior Publication Data

US 2009/0300810 A1    Dec. 10, 2009

Related U.S. Application Data

(63) Continuation of application No. 11/247,298, filed on Oct. 11, 2005, now Pat. No. 7,637,622.

(51) Int. Cl.
*G02B 27/00* (2006.01)

(52) U.S. Cl. ........................ 359/614; 359/601

(58) Field of Classification Search .................. 359/614, 359/601
See application file for complete search history.

(56) References Cited

U.S. PATENT DOCUMENTS

| | | |
|---|---|---|
| 2,423,320 A | 7/1947 | Hurley, Jr. |
| 2,761,046 A | 8/1956 | Herrick et al. |
| 3,137,784 A | 6/1964 | Kasemann |
| 3,245,315 A | 4/1966 | Marks et al. |
| 3,575,491 A | 4/1971 | Heilmeier |
| 3,731,986 A | 5/1973 | Fergason |
| 3,873,804 A | 3/1975 | Gordon |
| 3,881,808 A | 5/1975 | Gurtler et al. |
| 3,890,628 A | 6/1975 | Gurtler |
| 3,918,796 A | 11/1975 | Fergason |
| 3,967,881 A | 7/1976 | Moriyama et al. |
| 4,039,254 A | 8/1977 | Harsch |
| 4,071,912 A | 2/1978 | Budmiger |
| RE29,684 E | 6/1978 | Gordon |
| 4,093,832 A | 6/1978 | Isaacson et al. |
| 4,109,114 A | 8/1978 | Baer et al. |
| 4,143,264 A | 3/1979 | Gilbert et al. |
| 4,155,122 A | 5/1979 | Budmiger |

(Continued)

FOREIGN PATENT DOCUMENTS

DE    2315308    3/1972

(Continued)

OTHER PUBLICATIONS

K.H. Yang, *Two-Domain 80°-Twisted Nematic Liquid Crystal Display for Grayscale Applications*, Jpn. J. Applied Physics, vol. 31, pp. L1603-L1605, Part 2, No. 11B, Nov. 15, 1992.

(Continued)

*Primary Examiner*—Joshua L Pritchett
(74) *Attorney, Agent, or Firm*—Emily M. Van Vliet

(57) ABSTRACT

A protective automatic darkening filter (ADF) and an associated tool, such as a welding torch, are controlled by a corresponding communication unit. The invention helps to ensure that the tool is not activated before the ADF has reached its dark state. A communication channel between the communication unit and the ADF may be established using a wired or wireless medium.

12 Claims, 4 Drawing Sheets

U.S. PATENT DOCUMENTS

| | | | |
|---|---|---|---|
| 4,237,557 A | 12/1980 | Gordon | |
| 4,240,709 A | 12/1980 | Hornell | |
| 4,279,474 A | 7/1981 | Belgorod | |
| 4,328,493 A | 5/1982 | Shanks et al. | |
| 4,385,806 A | 5/1983 | Fergason | |
| 4,436,376 A | 3/1984 | Fergason | |
| 4,540,243 A | 9/1985 | Fergason | |
| 4,556,289 A | 12/1985 | Fergason | |
| 4,560,239 A | 12/1985 | Katz | |
| 4,664,479 A | 5/1987 | Hiroshi | |
| RE32,521 E | 10/1987 | Fergason | |
| 4,710,694 A | 12/1987 | Sutphin et al. | |
| 4,728,173 A | 3/1988 | Toth | |
| 4,759,608 A | 7/1988 | Yang | |
| 4,821,292 A | 4/1989 | Childress | |
| 4,844,569 A | 7/1989 | Wada et al. | |
| 4,853,973 A | 8/1989 | Boochard | |
| 4,863,244 A | 9/1989 | Fuerthbauer et al. | |
| 4,875,235 A | 10/1989 | Kuhlman | |
| 4,896,947 A | 1/1990 | Leenhouts | |
| 4,952,030 A | 8/1990 | Nakagawa et al. | |
| 5,015,086 A | 5/1991 | Okaue et al. | |
| 5,074,647 A | 12/1991 | Fergason et al. | |
| 5,113,270 A | 5/1992 | Fergason | |
| 5,140,707 A | 8/1992 | Johnson | |
| 5,184,156 A | 2/1993 | Black et al. | |
| 5,189,735 A | 3/1993 | Corona | |
| 5,191,468 A | 3/1993 | Mases | |
| 5,208,688 A | 5/1993 | Fergason et al. | |
| 5,248,880 A | 9/1993 | Fergason | |
| 5,252,817 A | 10/1993 | Fergason et al. | |
| 5,515,186 A | 5/1996 | Fergason et al. | |
| 5,533,206 A | 7/1996 | Petrie et al. | |
| 5,666,010 A | 9/1997 | Stratiotis | |
| 5,751,258 A | 5/1998 | Fergason et al. | |
| 5,825,441 A | 10/1998 | Hornell et al. | |
| 6,097,451 A | 8/2000 | Palmer et al. | |
| 6,185,736 B1 | 2/2001 | Ueno | |
| 6,734,393 B1 | 5/2004 | Friedl et al. | |
| D517,744 S | 3/2006 | Lee et al. | |
| D517,745 S | 3/2006 | Lee et al. | |
| D518,923 S | 4/2006 | Curran et al. | |
| D523,728 S | 6/2006 | Lee et al. | |
| D532,163 S | 11/2006 | Curran et al. | |
| 7,197,774 B2 | 4/2007 | Curran et al. | |
| 2004/0190106 A1 | 9/2004 | McLear et al. | |
| 2006/0101552 A1 | 5/2006 | Lee et al. | |
| 2006/0107431 A1 | 5/2006 | Curran et al. | |
| 2007/0081250 A1 | 4/2007 | Garbergs et al. | |

FOREIGN PATENT DOCUMENTS

| | | |
|---|---|---|
| DE | 35615 | 5/1979 |
| DE | 2742211 | 5/1984 |
| DE | 3842824 A1 | 6/1990 |
| DE | 3503958 | 5/1993 |
| EP | 0005417 B1 | 4/1979 |
| EP | 0157744 A1 | 10/1985 |
| EP | 0335056 A1 | 3/1988 |
| EP | 0349665 A1 | 1/1990 |
| FR | 84-038885 | 1/1984 |
| FR | 2530039 | 1/1984 |
| GB | 325586 | 2/1930 |
| JP | 55-92276 | 7/1980 |
| JP | 59-111102 | 6/1984 |
| JP | 4338732 | 11/1992 |
| RU | 2181213 | 4/2002 |
| RU | 2248022 | 3/2004 |
| SE | 7312733 | 4/1974 |
| SE | 7608690 | 2/1978 |
| SU | 1586705 A1 | 9/1986 |
| SU | 1586705 A | 8/1990 |
| WO | WO 88/05926 | 8/1988 |
| WO | WO 90/14611 | 11/1990 |
| WO | WO 90/14809 | 12/1990 |
| WO | WO 95/29428 | 11/1995 |
| WO | WO 97/15255 | 5/1997 |
| WO | WO 2004/053586 A1 | 6/2004 |
| WO | WO 2004/102265 A1 | 11/2004 |
| WO | WO 2007/025315 A1 | 3/2007 |

OTHER PUBLICATIONS

A. Dore et al., *P-21: Low Twist Nematic and PWM Direct Addressing as a New Technique for Large LCD Public Information Boards*, pp. 445-447, Eurodisplay, 2002.

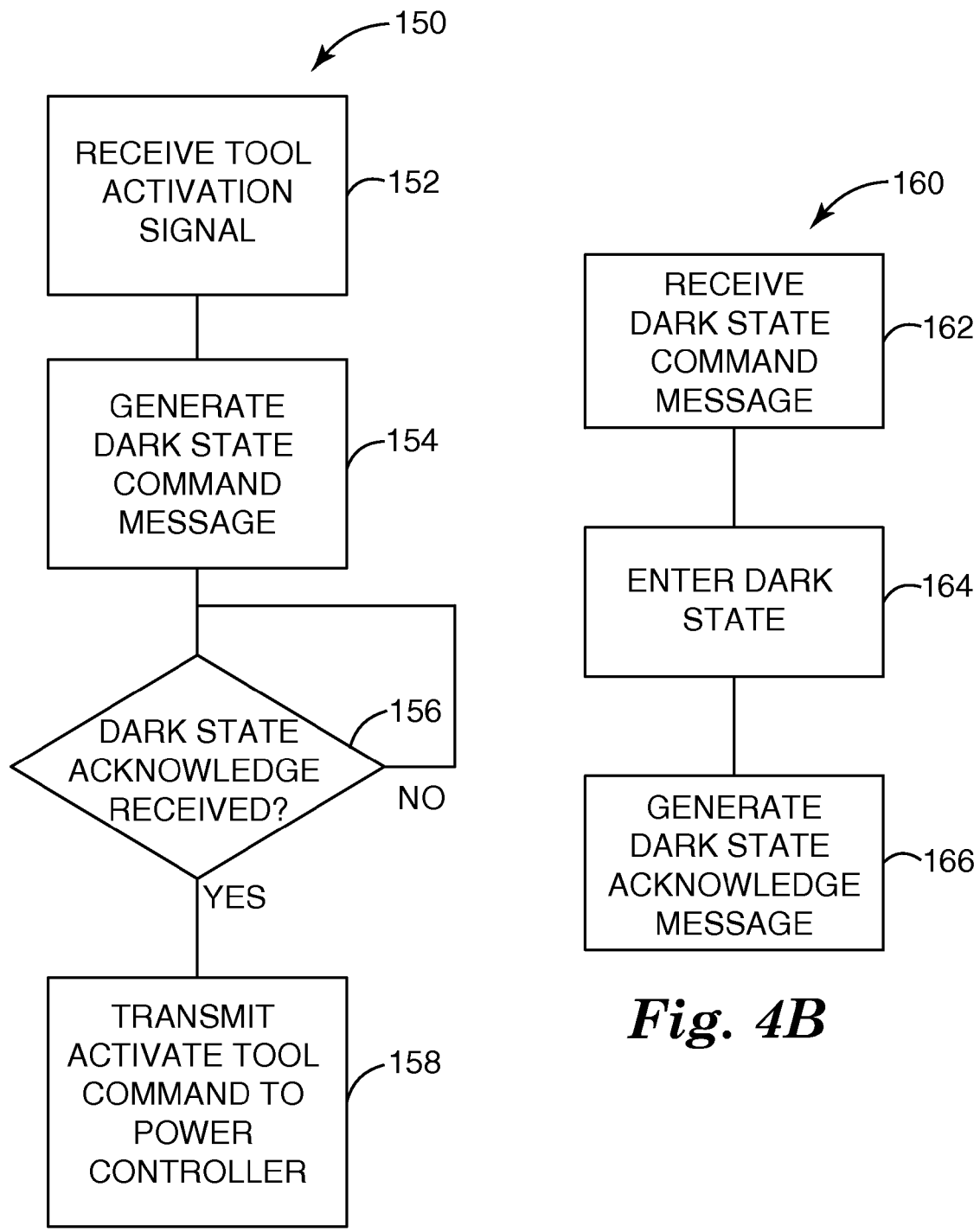

CONTROL OF AN AUTOMATIC DARKENING FILTER

CROSS-REFERENCE TO RELATED APPLICATION (1) This application is a continuation of U.S. Ser. No. 11/247,298, filed Oct. 11, 2005 now U.S. Pat. No. 7,637,622, the disclosure of which is incorporated by reference in its entirety herein.

The invention pertains to automatic darkening protective filter lens that is capable of changing from a light state to a dark state.

BACKGROUND

Automatic darkening filters, or ADFs, are often used for applications like welding where protection from intense levels of incident light, such as the glare of a welding arc, is desired. A typical ADF includes electronic control circuitry, powered by a battery, which causes the filter to change from a light (clear or transparent) state when not subjected to the glare of the welding arc to a dark (nearly opaque) state upon exposure to such glare. This enables a welder to perform a welding operation and also perform tasks outside the welding area without removing the protective shield.

Conventional ADFs include layers of liquid crystal material capable of changing from a light state to a dark state under control of a control voltage. A sensor detects the start of a welding arc and generates a corresponding control voltage which, when applied to the filter lens, causes it to change from a light state to a dark state. Because the arc is already switched on when the sensors react, the switching of the ADF has to be very short, e.g., less than a few hundred microseconds. This abrupt or "hard" transition between the light state and the dark state can be uncomfortable to the user, especially under working conditions where many light-to-dark transitions are experienced throughout the course of a typical work day.

The sensors in a conventional ADF may be adversely affected by interference from other light sources, other welding machines, currents, or magnetic fields in the vicinity, which could cause the ADF to enter the dark state in the absence of a welding arc. In certain applications—such as low current tungsten inert gas (TIG) welding—the usable signal from the welding arc is relatively weak. In these cases, the detector may fail to detect the arc, resulting in failure of the ADF to enter the dark state even in the presence of a welding arc.

SUMMARY OF THE INVENTION

The invention provides a protective automatic darkening filter (ADF) and an associated tool, such as a welding torch, which ADF and tool are controlled by a corresponding communication unit. The invention helps ensure that the tool is not activated before the ADF has reached its dark state. A communication channel between the communication unit and the ADF may be established using a wired or wireless medium.

In one embodiment, the invention is directed to a system comprising a switchable filter that changes from a light state to a dark state in response to a dark state command message, a power controller that provides power to a tool in response to an activate tool command, and a communication unit that generates the dark state command in response to a tool activation signal, wherein the switchable filter further generates a dark state acknowledge message upon entering the dark state, and wherein the communication unit further generates the activate tool command in response to the dark state acknowledge message.

In another embodiment, the invention is directed to a method that comprises: receiving a tool activation signal; generating a dark state command message for a switchable filter in response to the tool activation signal; receiving a dark state acknowledge message from the switchable filter; and generating an activate tool command in response to the dark state acknowledge message.

In another embodiment, the invention is directed to a method that comprises: receiving a tool activation signal; generating a dark state command message for a switchable filter in response to the tool activation signal; waiting for a dark state wait time to elapse; and generating an activate tool command after the dark state wait time has elapsed.

As used in this application, the term "automatic darkening filter" (ADF) means a protective device including circuitry and a switchable filter or lens that is designed to protect a user's eyes from excessive glare in an environment such as welding or in other environments where there is the potential for damage to the human eye from excessively bright light. The terms "switchable filter" and "ADF lens" mean a filter that is capable of changing from a light state to a dark state in response to a control signal.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 4A and 4B are flowcharts illustrating bidirectional control of an ADF entering the dark state in accordance with the present invention.

DETAILED DESCRIPTION OF PREFERRED EMBODIMENTS

Figure 1:
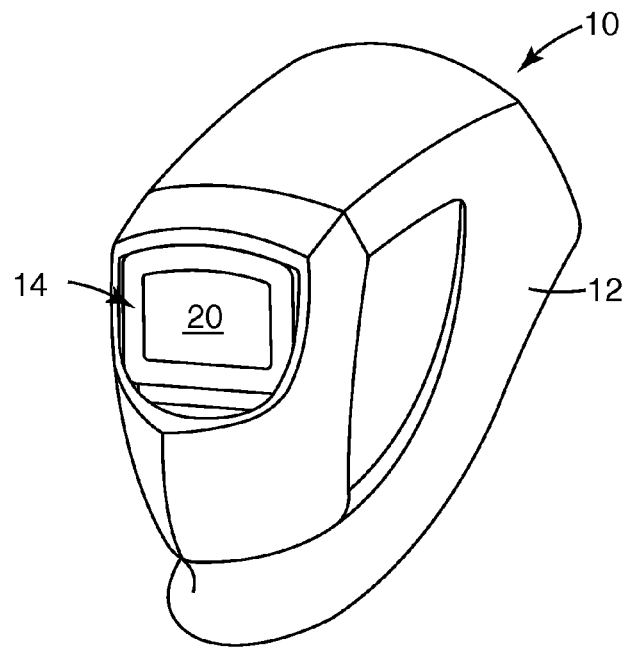
FIG. 1 is a perspective view of a welding helmet 10 that includes an automatic darkening filter (ADF) 14 that has a switchable filter lens 20 in accordance with the present invention.

FIG. 1 shows an example of a welding helmet 10 that includes a helmet body or shell 12 and an automatic darkening filter (ADF) 14. Specifically, the ADF 14 includes an auto-darkening filter lens 20 supported in the helmet shell 12. The auto-darkening filter lens 20 may be mounted in the helmet shell 12 so that it is directly in front of the wearer's eyes when the helmet is worn by the user. In one embodiment, the switchable lens 20 is replaceable. The lens 20 may include a rectangular (or other shaped) frame or housing. Examples of such filters are described in U.S. Pat. Nos. 6,097,451 and 5,825,441, both to Hörnell and Palmer. Examples of helmet shells may be seen, for example, in U.S. Pat. Nos. 6,185,739, 5,533,206, 5,191,468, 5,140,707, 4,875,235, and 4,853,973. The helmet 12 also may have clean air supplied to the interior, and thus may include a face seal to separate a breathing zone from the ambient air. An example of such a face seal is shown in U.S. patent application Ser. Nos. 10/987,512, 10/987,641, 10/988,789, 29/217,155, 29/217,153, 29/217,154, 29/217,107, and 29/217,156.

Figure 2:
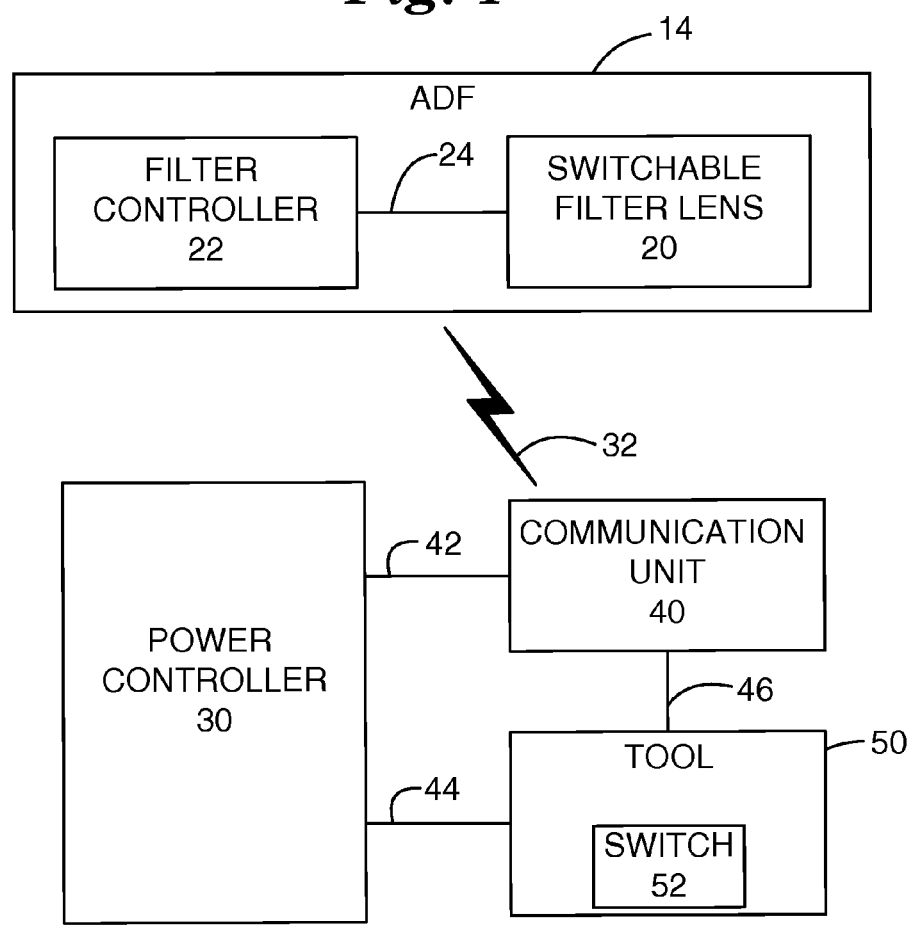
FIG. 2 is a block diagram of an ADF system in which an ADF 14 and an associated tool 50 are controlled by a corresponding communication unit 40 in accordance with the present invention.

FIG. 2 illustrates a block diagram of an ADF system that includes an ADF 14, a tool 50, a power controller 30, and a communication unit 40. The ADF 14 includes a switchable filter lens 20 that is capable of changing from a light state to a dark state. Control of switchable filter lens 20 is provided by filter control electronics 22 via connection 24. In one embodiment, switchable filter lens 20 may be a laminate of several different layers including, for example, UV/IR filters, polarizers, and liquid crystal elements. In other embodiments, switchable filter lens 20 may be constructed using electro chrominance filters. Switchable filter lens 20 acts as a shutter that darkens in response to a control signal to shade the lens and thereby protect the user's eyes from harmful glare resulting from operation of tool 50, such as the glare of a welding arc produced from operation of a welding torch. Examples of suitable switchable filters are described in U.S. Pat. Nos. 6,097,451 and 5,825,441, and in copending and commonly assigned U.S. patent application Ser. No. 11/076,081 to Magnusson et al., filed Mar. 9, 2005.

Tool 50 may include, for example, a welding torch or other type of machine tool or power tool. Tool 50 may be any kind of power or machine tool of the types used in many different industries—for example, carpentry tools, plumbing tools, or machine tools of other trades—and it shall be understood that the invention is not limited in this respect. For purposes of illustration, however, the invention is described as it applies to tools used in the welding industry, such as welding torches. Power controller 30 contains the necessary power control electronics necessary to provide energy to tool 50.

The invention provides a protocol between the ADF 14 and a communication unit 40 to ensure that tool 50 is not activated until the ADF 14 has entered the dark state. A communication channel 32, which may be either unidirectional or bidirectional, provides for communication between the ADF 14 and the communication unit 40. FIG. 2 shows the communication channel 32 as a wireless communication channel, although the communication channel 32 may also be provided via a wired connection. Wireless communication may be provided using any of the many known wireless communication methods, such as infra-red communication, radio frequency (RF) communication, or acoustical communication, or by any suitable later-developed technology. Command lines 42, 44, and 46 allow communication between communication unit 40, power controller 30, and tool 50.

Messages that are transmitted between communication unit 40 and the ADF 14 are used to control the transition of lens 20 from the light state to the dark state and vice versa. These messages also control activation of tool 50. In this way, the system ensures that lens 20 is in the dark state before it allows activation of tool 50. In a welding environment, for example, in which tool 50 would be a welding torch, communication unit 40 ensures that the lens 20 is in the dark state before power controller 30 is allowed to ignite the welding arc. Although communication unit 40 is shown as a separate component in FIG. 2, the functionality of the communication unit also may be located within tool 50, between a cable connecting tool 50 with power controller 30, within power controller 30, or other suitable position depending upon the particular application and environment in which the system is to be used.

In addition to state change commands from communication unit 40 and state acknowledges from ADF 14, the messages transmitted between the ADF 14 and the tool controller 60 through the communication channel 32 may also include other information. For example, the system may ensure that each ADF is associated with one and only one tool via unique identity codes embedded within the messages transmitted in the communication channel 32. To this end, each ADF 20 may be uniquely associated with one tool 50 via at least one unique identity code transmitted in the dark state command message. A unique association between ADF 20 and tool 50 and/or communication unit 40 may help ensure that interference from other sources of light, currents, or magnetic fields will not effect the operation of the ADF, causing it to darken or lighten inappropriately.

The tool 50 can include at least one switch 52 through which a user controls the start and stop of tool 50. In a welding environment, for example, a welder controls the start and stop of the welding arc by pressing or releasing one or more switch(es) located on the welding torch. Switch 52 may include, for example, push buttons, a trigger, other user actuated switch, or some combination thereof.

Actuation of switch 52, either activating or deactivating (e.g., pressing or releasing) produces a resulting tool activation signal. As used in this description, the term "tool activation signal" refers to any actuation of switch 52, whether to activate the tool, deactivate the tool, or adjust the amount of power applied (e.g., to adjust the speed, torque, or intensity of the tool) of the tool.

The tool activation signals resulting from actuation of switches 52 are received by communication unit 40 via connection 46. In response to the tool activation signals, the communication unit 40 may communicate with the ADF 14 via communication channel 32 to ensure that the ADF lens is changed to the proper state and then allow power controller 30 to act accordingly. In this way, the ADF system ensures that tool 50 is not activated before ADF 20 has entered its dark state and that the user's eyes will not go unprotected.

The system may also result in improved reliability in certain situations. For example, each ADF may be associated with a particular tool controller via unique identity codes embedded in the messages transmitted via communication channel 32. This configuration ensures that other welding machines in the neighborhood cannot influence the operation of a particular ADF. Interference from other light sources, currents, or magnetic fields will not affect the ADF operation. In addition, detection of low current TIG welding can be more reliable when the system utilizes a command message rather than a weak photodiode signal to detect the start of a welding arc.

Figure 3A:
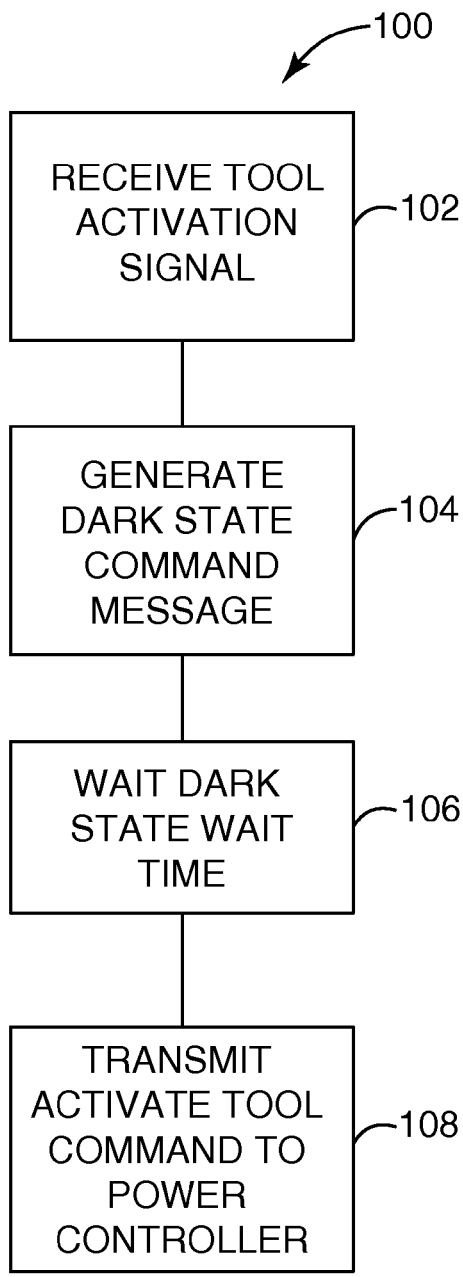
FIGS. 3A and 3B are flowcharts illustrating unidirectional control of an ADF in accordance with the present invention.
Figure 3B:
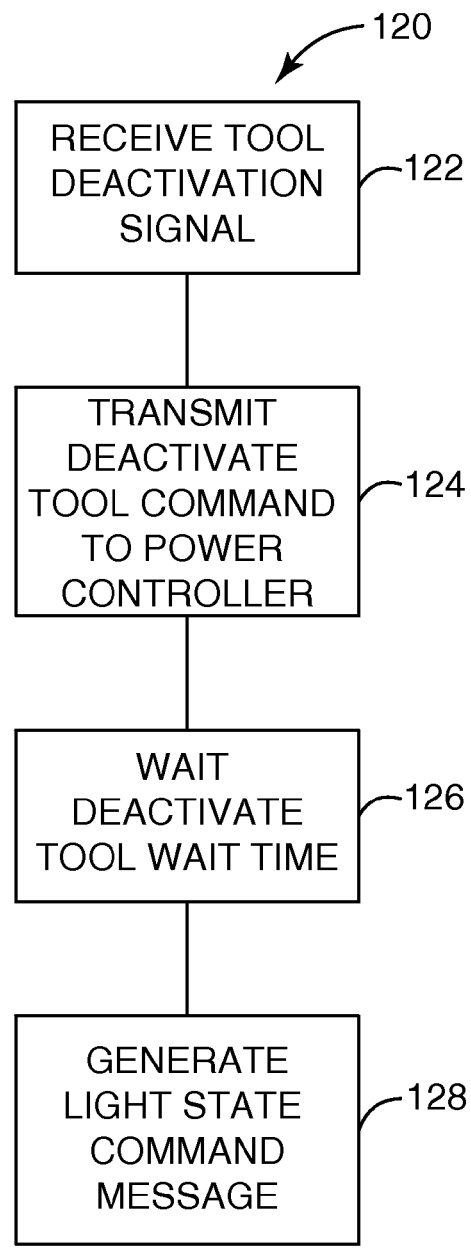

FIGS. 3A and 3B are flowcharts illustrating unidirectional control of an ADF. These charts are described with the identifying numerals in the figures for the process steps being presented in parentheses. The identifying numerals used in the text that are not in parenthesis refer to structural parts shown in FIGS. 1 and 2. FIGS. 3A and 3B show both the process carried out by communication unit 40 for controlling the transition from the light state to the dark state (100) and the process carried out by communication unit 40 for controlling the transition from the dark state to the light state (120). Control of the transition from the light state to the dark state (100) begins when communication unit 40 receives a tool activation signal from tool 50 (102). The tool activation signal may be user generated by, for example, actuation of one of switches 52 located on tool 50. In response to the tool activation signal, communication unit 40 generates a dark state command message (104). The dark state command message may include, for example, a command instructing the ADF to enter the dark state as well as unique identity code(s) identifying the communication unit 40 and the associated ADF 20 to which the dark state command is directed.

After generating the dark state command message, communication unit 40 waits a predetermined length of time sufficient to allow the ADF lens 20 to enter the dark state (the dark state wait time) (106). The dark state wait time may be less than 1 second, and further may be anywhere between 1 millisecond and 900 milliseconds, for example. After the dark state wait time has elapsed, communication unit 40 transmits an activate tool command to power controller 30 (108). In one embodiment, communication unit 40 may repeat the dark state command message one or more times during the dark state wait time. If the first dark state command message was not received correctly, the lens 20 will have another chance to properly receive and respond to the command when the dark state command message is retransmitted. Each retransmission during the wait will increase the probability for a successful message receipt.

Transition control from the dark state to the light state (120) begins when communication unit 40 receives a tool deactivation signal from tool 50 (122). This tool deactivation signal may be user generated by, for example, actuation (pressing a pushbutton, releasing a pushbutton or trigger, etc.) of one of switches 52 located on tool 50. In response to the tool deactivation signal, communication unit 40 transmits a deactivate tool command to power controller 30 (124).

After transmitting the deactivate tool command, communication unit 40 waits a predetermined length of time sufficient to allow power controller 30 to deactivate tool 50 (the deactivate tool wait time) (126). The deactivate tool wait time typically is less than 1 second, and may be anywhere between 1 millisecond and 900 milliseconds, for example. After the deactivate tool wait time has elapsed, communication unit 40 generates and transmits a light state command message to the ADF 14 (128). Again, the light state command message may include a command instructing the ADF to enter the light state as well as a unique identity code(s) identifying the communication unit and the associated lens 20 to which the light state command is directed. The light state command causes the ADF lens 20 to transition from the dark state to the light state.

FIGS. 4A and 4B are flowcharts illustrating bidirectional control of an ADF lens as it transitions from the light state to the dark state. FIG. 4A shows a process (150) followed by communication unit 40 and FIG. 4B shows a process (160) followed by ADF 20 during a bidirectional handshaking protocol. In response to receipt of a tool activation signal (152), the communication unit 40 generates and transmits a dark state command message via communication channel 32 (154). Communication unit 40 waits to receive a dark state acknowledge message (156) from the ADF 14 via communication channel 32, indicating that the ADF lens 20 has completed the transition from the light state to the dark state. In response to the dark state acknowledge message from the ADF 14, the communication unit 40 transmits an activate tool command to power controller 30, thus causing power to be applied to tool 50.

On the ADF 14 side of the protocol (160), upon receipt of the dark state command message (162), the filter controller 22 applies a corresponding control voltage to switchable filter 26, causing it to enter the dark state (164). Once the lens 20 completes its transition to the dark state, the lens 20 transmits the dark state acknowledge message via communication channel 32 (166). As described above, the dark state command message and the dark state acknowledge message may include unique identity code(s) uniquely associating lens 20 and communication unit 40 as well as the dark state command and dark state acknowledge.

Figures 5A, 5B:
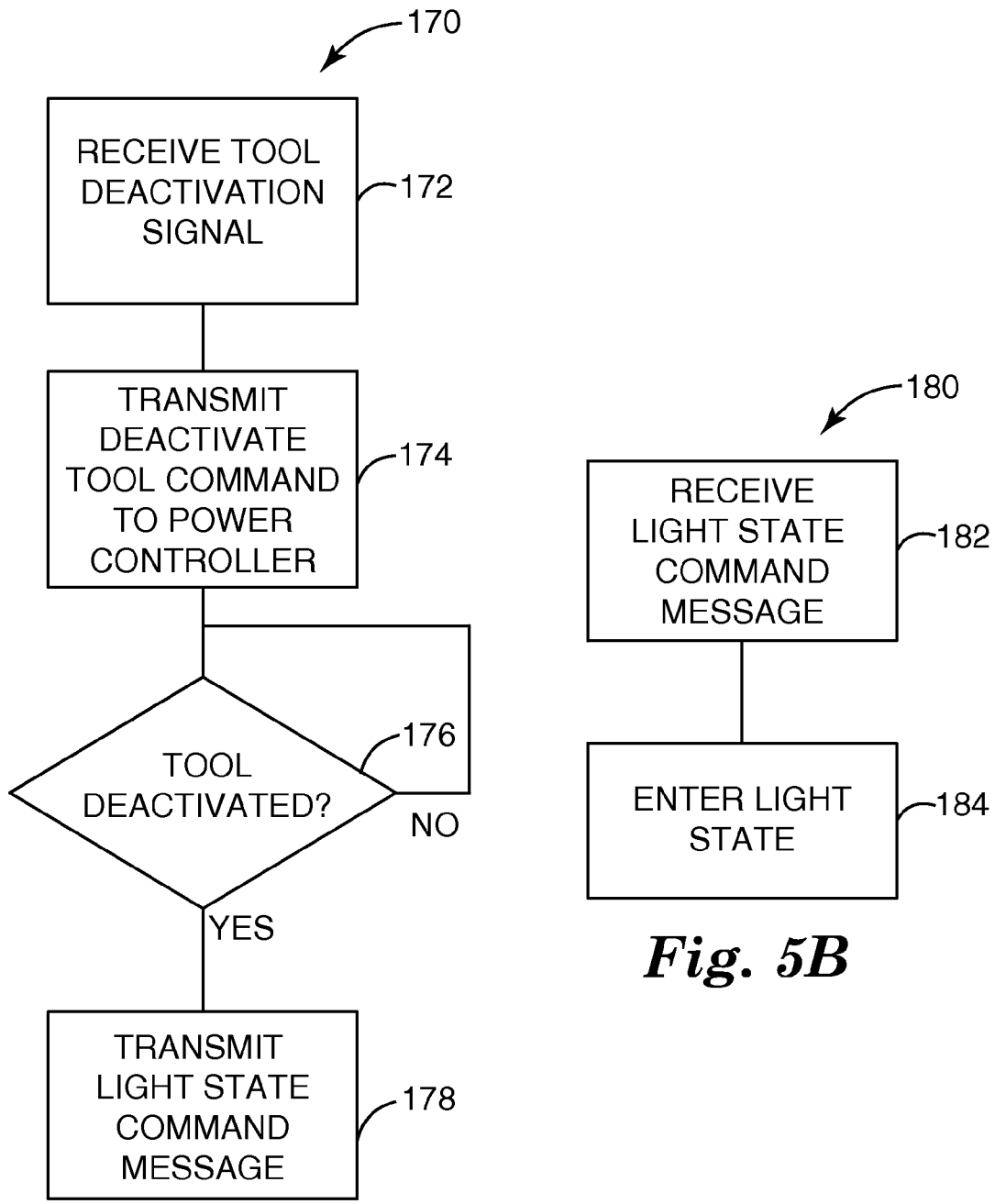
FIGS. 5A and 5B are flowcharts illustrating bidirectional control of an ADF entering the light state in accordance with the present invention.

FIGS. 5A and 5B are flowcharts illustrating bidirectional control of the transition of an ADF 14 from the dark state to the light state. FIG. 5A shows a process (170) followed by communication unit 40 and FIG. 5B shows a process (180) followed by ADF 14 during a bidirectional handshaking protocol. In response to receipt of a tool deactivation signal (172), communication unit 40 generates a deactivate tool command to power controller 30 (174). Communication unit 40 then waits until tool 50 has been deactivated (176) indicating that power has been removed from tool 50. When the tool has been deactivated (176), communication unit 40 generates and transmits a light state command message via communication channel 32 (178). On the ADF 14 side of the protocol (180), upon receipt of the light state command message (182) filter controller 22 applies an appropriate control voltage to switchable filter 26, causing it to transition to the light state (184).

In this manner, ADF 14 and communication unit 40 cooperate to ensure that tool 50 is not activated before the ADF lens 20 has entered the dark state. Because the ADF and the communication may be uniquely associated with one another via unique identity codes, the invention may help ensure that the operation of the ADF is not influenced by other tools in the vicinity, or by interference from other sources of light, currents, or magnetic fields.

The ADF system described herein may result in improved reliability and relaxed requirements on the switching time of the ADF 14. For example, the ADF lens 20 may enter the dark state more slowly. Because the tool is not activated until a dark state is achieved, activation of the tool may be delayed for an arbitrary length of time (generally some number of milliseconds, such as anywhere between 1 millisecond and 900 milliseconds) allowing enough time for the lens to go completely dark. This means that a "soft" change from light to dark state may be utilized. A smooth transition from light to dark state is more comfortable for the user's eyes than an abrupt change. Also, slower technologies, such as electro chrominance technology, may be used for the switchable filter. Advantages offered by electro chrominance technology may include a "lighter" light state, the potential for better optical characteristics, and lower cost.

The invention may also help to ensure that the ADF is not adversely affected by interference from other sources of light, other welding machines in the vicinity, currents, or magnetic fields that could cause the ADF to enter the dark state even in the absence of a welding arc. Further, the transition to the dark state does not rely on sensing of a welding arc or other source of incident light from which the user is to be protected. Thus, the danger of failing to enter the dark state in those applications where the welding arc signal is weak is reduced or eliminated. Thus, the invention helps to ensure that the ADF provides proper protection to a user in a wide variety of situations and environments.

All of the patents and patent applications cited above, including those cited in the Background Section, are incorporated by reference into this document in there respective entireties.

Various embodiments of the invention have been described. For example, a system comprising an ADF and associated tool have been described ensure that the tool is not activated before the ADF has reached its dark state. Nevertheless, various modifications may be made to the system described herein without departing from the spirit and scope of the invention. For example, although primarily described in the context of welding, the invention may have broad application for a wide variety of other systems or fields. These and other embodiments are within the scope of the following claims.

The invention claimed is:

1. A system, comprising:
   a switchable filter comprising an electro chrominance filter;
   a communication unit; and
   a power controller;
   wherein the switchable filter changes from a light state to a dark state after receiving a dark state command message from the communication unit, and generates and transmits a dark state acknowledge message to the communication unit upon entering the dark state;
   wherein the communication unit generates and transmits the dark state command message to the switchable filter after receiving a tool activation signal, waits to receive the dark state acknowledge message from the switchable filter, and generates and transmits an activate tool command to the power controller after receiving the dark state acknowledge message from the switchable filter; and
   wherein the power controller activates a welding tool after receiving the activate tool command.

2. The system of claim 1, wherein the switchable filter changes from the dark state to the light state after receiving a light state command message.

3. The system of claim 1, wherein the communication unit transmits the dark state command message and receives the dark state acknowledge message via a wireless communication channel.

4. The system of claim 3, wherein the light state command message includes a unique identity code.

5. The system of claim 1, wherein the switchable filter is positioned within a safety helmet.

6. The system of claim 1, wherein at least one of the dark state command message and the dark state acknowledge message includes a unique identity code.

7. The system of claim 1, wherein the communication unit and the switchable filter are associated with one another via unique identity codes.

8. The system of claim 1, wherein the tool is activated 1 to 100 milliseconds after the switchable filter has entered the dark state.

9. The system of claim 1, wherein the communication unit further generates and transmits a deactivate tool command after receiving a tool deactivation signal; and wherein the power controller deactivates the tool after receiving the deactivate tool command.

10. The system of claim 1, wherein the switchable filter changes from the light state to the dark state in response to a change in an applied voltage.

11. An automatic darkening filter (ADF) system comprising:
    a helmet;
    a switchable filter, comprising an electro chrominance filter, mounted in the helmet and capable of changing from a light state to a dark state without reliance on sensing of incident light, the switchable filter further capable of generating and transmitting a dark state acknowledge message after entering the dark state; and
    a filter controller that upon receipt of a dark state command message applies a corresponding control voltage to the switchable filter causing it to enter the dark state, and upon receipt of a light state command message applies a corresponding control voltage to the switchable filter causing it to enter the light state.

12. The ADF system of claim 11, wherein the switchable filter generates a wireless dark state acknowledge message.

* * * * *